United States Patent [19]
Hague et al.

[11] Patent Number: 5,382,232
[45] Date of Patent: Jan. 17, 1995

[54] INFUSION SYSTEM WITH AIR-IN-LINE CLEAR FUNCTION

[75] Inventors: Clifford W. Hague, Canyon Country; Paul A. Koenig, Valencia, both of Calif.

[73] Assignee: Ivac Corporation, San Diego, Calif.

[21] Appl. No.: 852,622

[22] Filed: Mar. 13, 1992

[51] Int. Cl.⁶ ............... A61M 31/00; A61M 1/00
[52] U.S. Cl. .................................. 604/65; 604/67; 604/123; 128/DIG. 13
[58] Field of Search ............ 604/65, 67, 151, 122-125; 73/19.01; 128/DIG. 13

[56] References Cited

U.S. PATENT DOCUMENTS

| | | | |
|---|---|---|---|
| 4,114,144 | 9/1978 | Hyman | 128/DIG. 13 X |
| 4,217,993 | 8/1980 | Jess et al. | 604/65 X |
| 4,321,461 | 3/1982 | Walter, Jr. et al. | 604/65 X |
| 4,570,639 | 2/1986 | Miodonnik | 604/65 X |
| 4,658,244 | 4/1987 | Meijer | 128/DIG. 13 X |
| 4,673,927 | 6/1987 | Cianciavicchia et al. | 604/65 X |
| 4,762,518 | 8/1988 | Kreinick | 604/65 X |
| 4,764,166 | 8/1988 | Spani | 604/65 |
| 4,784,643 | 11/1988 | Siretchi et al. | 604/65 X |
| 4,829,448 | 5/1989 | Balding et al. | 128/DIG. 13 X |
| 4,856,339 | 8/1989 | Williams | 128/DIG. 13 X |
| 4,950,235 | 8/1990 | Slate et al. | 604/65 |
| 4,959,050 | 9/1990 | Bobo, Jr. | 604/67 X |
| 5,006,110 | 4/1991 | Garrison et al. | 604/65 |
| 5,041,086 | 8/1991 | Koenig et al. | 128/DIG. 13 X |
| 5,059,171 | 10/1991 | Bridge et al. | 604/67 |
| 5,064,412 | 11/1991 | Henke et al. | 604/65 |
| 5,102,392 | 4/1992 | Sakai et al. | 128/DIG. 13 X |
| 5,103,211 | 4/1992 | Daoud et al. | 604/67 X |
| 5,123,275 | 6/1992 | Daoud et al. | 128/DIG. 13 X |
| 5,176,631 | 1/1993 | Koenig | 604/65 |
| 5,177,993 | 1/1993 | Beckman et al. | 128/DIG. 13 X |

FOREIGN PATENT DOCUMENTS 8200591 3/1982 WIPO ............ 128/DIG. 13

Primary Examiner—Randall L. Green
Assistant Examiner—Elizabeth M. Burke
Attorney, Agent, or Firm—Fulwider, Patton, Lee & Utecht

[57] ABSTRACT

An infusion system with an air-in-line sensor is provided with improved apparatus and method for quickly and easily clearing small quantities of undissolved gas such as air from the sensor detection field. The infusion system includes an infusion pump having control components responsive to the air-in-line sensor to activate an alarm and/or to cease pump operation when undissolved gas is detected. A "clear air" key or switch is provided on the pump for actuation by medical personnel to operate the pump in a manner delivering a small pulse of the infusion liquid to move a small detected quantity of gas past the air-in-line sensor. The system can be adapted for actuation of the "clear air" key up to a selected number of times, while monitoring and accumulating the total fluid quantity delivered to a patient.

16 Claims, 6 Drawing Sheets

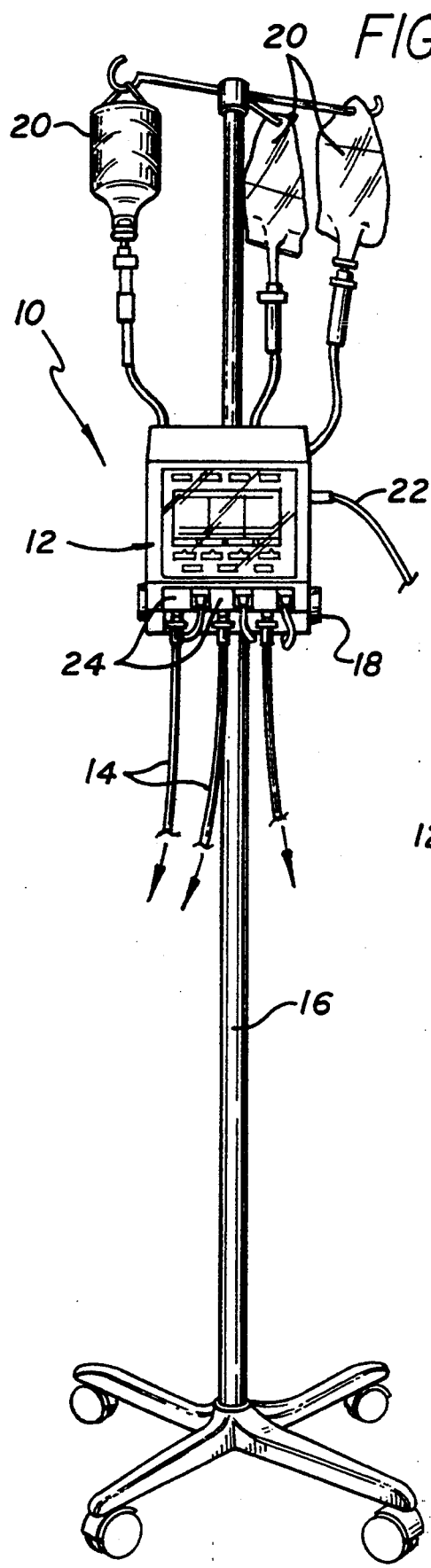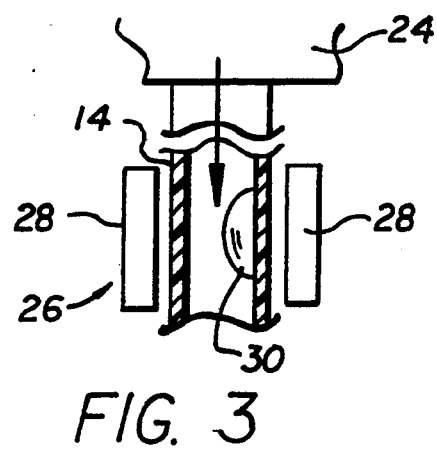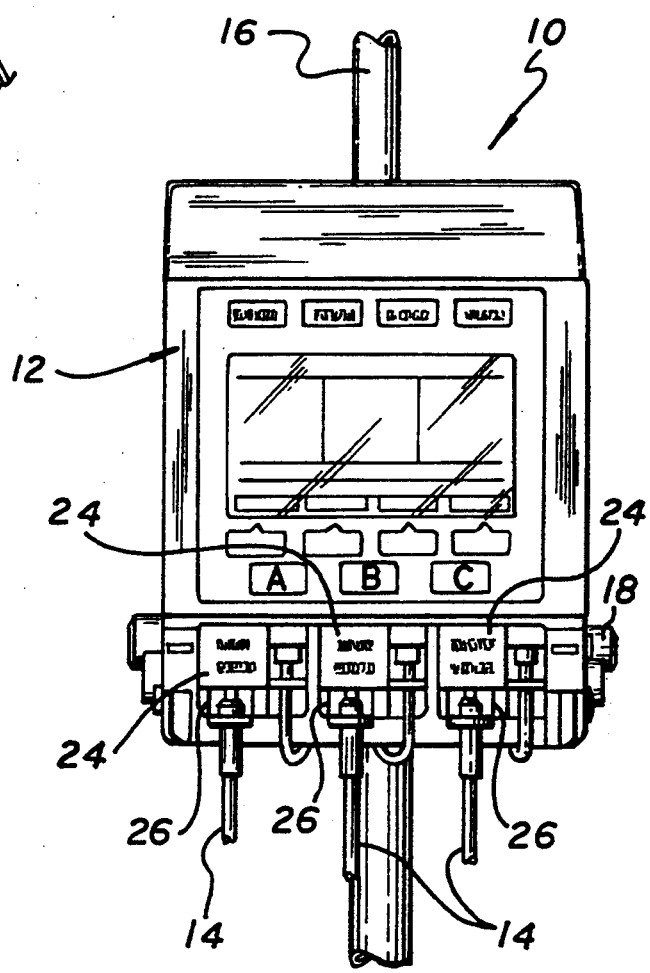

INFUSION SYSTEM WITH AIR-IN-LINE CLEAR FUNCTION

This application is related to a concurrently filed copending patent application. This patent application is U.S. Ser. No. 07/852,616, entitled "Restrictor Fitting for an Infusion Pump," which application is hereby incorporated herein by reference,

BACKGROUND OF THE INVENTION

Field of the Invention

The present invention relates generally to medical fluid infusion systems for delivering a selected medical fluid to a patient, and more particularly to an improved apparatus and method for quickly and easily clearing small quantities of detected air or gas from the detection field of an air-in-line sensor in a patient fluid infusion system.

Medical fluid infusion systems are generally known in the art for use in delivering one or more selected fluids through appropriate tubing and/or a catheter or the like to a patient. Such infusion systems often utilize a relatively compact electronically controlled pump adapted for mounting onto a conventional portable medical equipment pole and including an appropriate pump element or elements for closely regulating fluid delivery to the patient. One example of an infusion pump of this general type is marketed by MiniMed Technologies of Sylmar, Calif. under the name MiniMed III.

Modern infusion pumps used in patient fluid infusion systems are commonly equipped with an air-in-line sensor for monitoring fluid delivery through a length of tubing and to activate an alarm and/or disable the pump upon detection of air. In this regard, ultrasonic detectors are known in the art and have the capability to determine the volume of air in a tubing line and to activate the alarm or halt pump operation when the detected air volume exceeds a predetermined and potentially harmful threshold. Such air detectors may operate in conjunction with the pump to decrement an accumulated fluid infusion record in accordance with the volume of air bubbles detected in the infusion tubing line.

Relatively small air or gas bubbles may commonly occur at the discharge side of the pump element, apparently as a result of outgassing at that location. Accordingly, the detection field of the air-in-line sensor is typically located at the discharge side of the pump element to insure detection of air within the infusion line. In most instances, the volume of air or gas present at the discharge side of the pump is sufficiently small such that no significant patient hazard results and there is no need to interrupt pump operation. Instead, the threshold setting for the air-in-line sensor is simply adjusted to allow continued pump operation when small air volumes are detected.

In some instances, however, small air bubbles can temporarily stick along the tubing line without obstructing continued fluid flow to the patient. When this occurs within the detection field of the air-in-line sensor, the sensor will detect the small bubble or bubbles as an elongated and thus significantly greater air volume, whereby the sensor will respond to activate the alarm or to halt pump operation. In this event, it is necessary for nursing personnel or the like to conduct a visual check of the infusion system and, if the actual volume of detected air or gas is medically insignificant, manipulate the infusion tubing and/or the pump element to clear the air from the detection field of the sensor so that the pump can be restarted. Such manipulation of the infusion tubing typically involves manual tapping or shaking of the infusion tubing line and/or pump components connected thereto to dislodge and move stuck air bubbles to a location downstream of the air-in-line sensor. False alarms of this type can occur on several occasions throughout the course of a nursing shift, and are viewed by nursing personnel as a significant nuisance.

The present invention provides a significant improvement in medical fluid infusion systems by adapting the infusion pump for rapid clearing of small quantities of air or gas from the detection field of an air-in-line sensor, without requiring significant manual handling of system components.

SUMMARY OF THE INVENTION

In accordance with the invention, an infusion system for infusing a medical liquid or liquids to a patient includes a "clear air" key or switch which can be actuated by medical personnel when required to clear a small bubble or bubbles of air or gas from the detection field of an air-in-line sensor. The "clear air" key, when actuated, operates the infusion pump to deliver a small output pulse of the medical liquid for dislodging the air or gas from the detection field of the air-in-line sensor by displacing the gas to a downstream location along a length of infusion tubing.

In the preferred form, the infusion pump includes one or more pump elements adapted for controlled delivery of one or more medical fluids from a respective reservoir source to a patient, wherein each pump element includes an air-in-line sensor such as an ultrasonic air detector for monitoring air or gas along the infusion tubing at a discharge side of the pump element. The air sensor is designed for adjustable response in accordance with the detected quantity of air or gas to activate a pump alarm and/or to disable pump operation. For example, the air sensor can be calibrated to activate the alarm only upon detection of a predetermined minimum air volume, or to activate the alarm in conjunction with pump disablement upon detection of a higher predetermined maximum air volume. One example of a fluid infusion pump of this type is marketed by MiniMed Technologies of Sylmar, Calif. under the name MiniMed III.

In accordance with the invention, the infusion pump includes the "clear air" key for selective actuation by medical personnel to clear a small quantity of air from the detection field of the air sensor when the pump is in an alarm or stop mode. The "clear air" key is particularly intended for quickly and easily clearing a small air bubble or bubbles which have become stuck within the sensor detection field and have been misinterpreted by the sensor as a larger and potentially harmful air volume. Actuation of the "clear air" key operates the infusion pump to deliver a small volume pulse or bolus of infusion liquid to displace the small air volume to a downstream location beyond the sensor detection field, so that the normal pump infusion operation can be restarted. In the preferred form, the "clear air" key is enabled whenever the sensor detects the predetermined minimum volume of undissolved gas along the infusion line, whereupon the "clear air" key can be actuated a selected multiple number of times to dislodge the air or gas from the detection field of the air sensor, while including the fluid pulse or pulses within an accumulated infusion record.

Other features and advantages of the present invention will become more apparent from the following detailed description, taken in conjunction with the accompanying drawings which illustrate, by way of example, the principles of the invention.

DESCRIPTION OF THE DRAWINGS

These and other advantages of the present invention are best understood with reference to the drawings, in which:

FIG. 1 is a front perspective view illustrating a medical fluid infusion pump adapted to include a clear air function embodying the novel features of the invention;

FIG. 2 is an enlarged and fragmented front elevational view of the infusion pump of FIG. 1;

FIG. 3 is a further enlarged and somewhat schematic sectional depiction of an air bubble disposed within the detection field of an air-in-line sensor;

DETAILED DESCRIPTION OF THE PREFERRED EMBODIMENT

Figure 4:
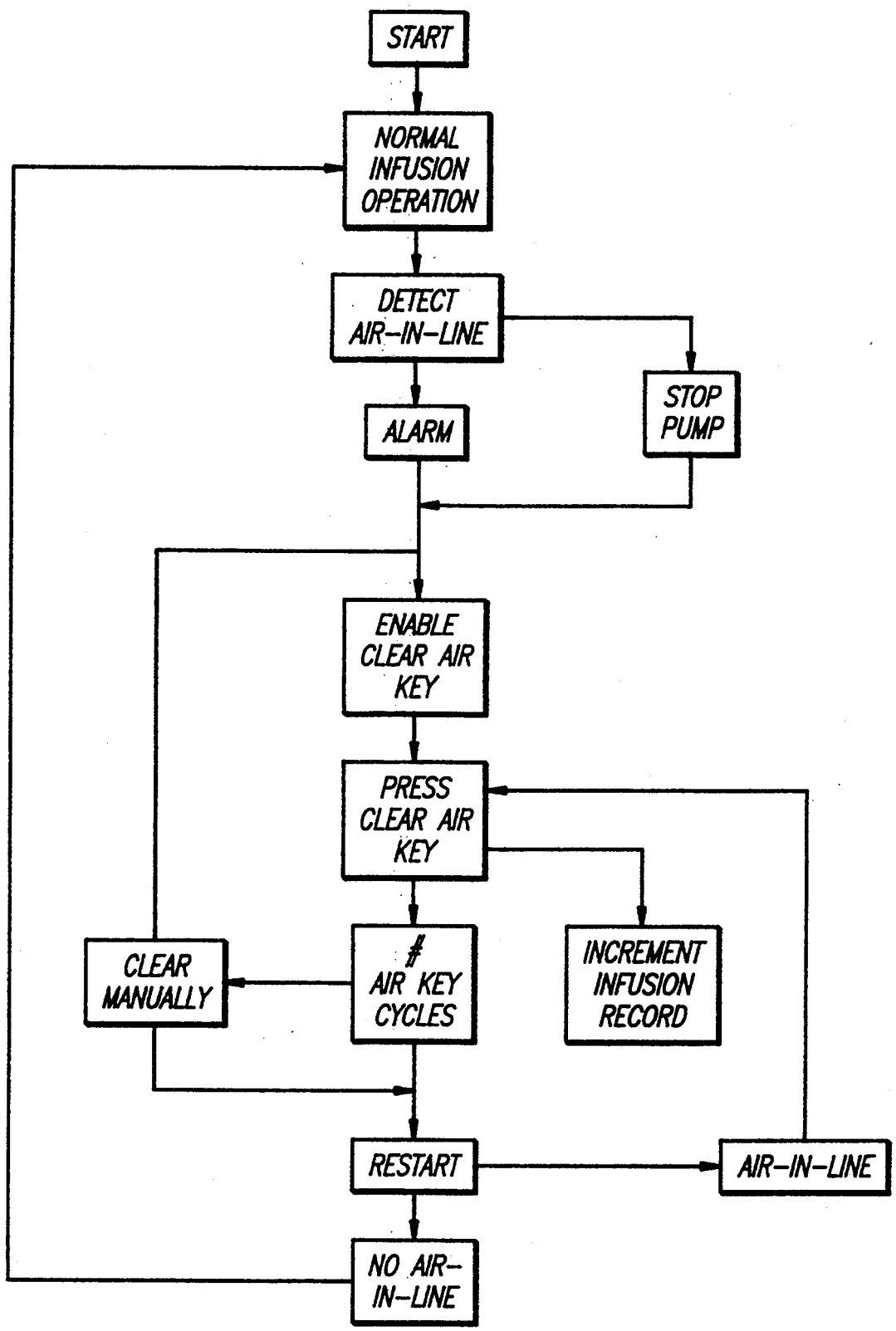
FIG. 4 is a flow chart depicting operation of the infusion pump clear air function, in accordance with the invention.

As shown in the exemplary drawings, a medical fluid infusion system referred to generally in FIG. 1 by the reference numeral 10 is provided for delivering one or more medical liquids to a patient (not shown) under controlled, closely regulated conditions. The infusion system 10 includes an infusion pump 12 for delivering the medical liquid or liquids through infusion tubing 14 to the patient. The infusion pump 12 is designed, in accordance with the invention, to include a "clear air" key or switch which can be manually actuated by medical personnel to deliver a small fluid pulse from the pump, for purposes of clearing a small quantity of air from the detection field of an air-in-line sensor.

FIGS. 1 and 2 illustrate the infusion pump 12 in the form of a compact instrument adapted for mounting onto a conventional medical equipment pole 16 by means of an appropriate adjustable clamp bracket 18 or the like. The illustrative infusion pump 12 includes multiple parallel fluid delivery channels for independent programming control to regulate administration of one or more medical liquids from appropriate reservoirs 20 via the infusion tubing 14 to a patient. Electronic control components and associated mechanical pumping devices are integrated into the pump 12 and normally operated upon connection of the instrument to an appropriate power supply as by means of a power cord 22. In a preferred form, the infusion pump 12 comprises a compact and multiple channel pump adapted for operation with disposable pump elements or cassettes 24, of the type utilized in the MiniMed III fluid infusion pump marketed by MiniMed Technologies, Sylmar, Calif. A more detailed disclosure of the construction and operation of the MiniMed III pump is found in U.S. Pat. No. 5,000,663, which is incorporated by reference herein.

In a fluid infusion pump 12 of this general type, each pump element 24 is normally associated with an air-in-line sensor 26 for monitoring the liquid at the discharge side of the pump element for the presence of air or gas. In this regard, such air-in-line monitoring is necessary or desirable to prevent infusion of potentially harmful quantities of air or gas into the patient. The air-in-line sensor 26 typically includes optical or ultrasonic means to detect the presence of undissolved air or gas bubbles in the liquid stream at the discharge side of the associated pump element 24, and for responding to the detected gas to activate a visual and/or audio pump alarm, and/or to halt operation of the corresponding pump channel. For example, air-in-line sensors of the ultrasound type can be calibrated to place the pump 12 in an alarm mode when a predetermined, potentially harmful volume of air or gas is detected, or to place the pump 12 in a stop mode when a larger predetermined gas volume is detected.

As shown in FIG. 3 with respect to a single pump channel, each air-in-line sensor 26 comprises a pair of appropriate sensor elements 28 mounted on the pump in a position straddling a short length of the infusion tubing 14 disposed in close proximity to the discharge side of the associated pump element 24. Medical fluid in liquid form is normally discharged from the pump element 24 at a closely regulated rate which is monitored and recorded by electronic components within the pump instrument. Small, medically insignificant quantities of air or gas can occur in the form of one or more small air bubbles 30 particularly at the discharge side of the pump element 24 wherein such small volume can normally be permitted to flow with the infusion liquid through the sensor detection field for ultimate infusion into the patient. Modern infusion pumps may include the capability to decrement an accumulated infusion record in accordance with the volume represented by air or gas bubbles passing through the sensor detection field.

However, it is possible for one or more small air bubbles 30 (FIG. 3) to stick or become trapped along the tubing 14 and within the detection field of the air-in-line sensor 26, whereupon such trapped bubble will be detected by the sensor 26 as a significantly larger gas volume of elongated shape flowing through the detection field. When this occurs, the air-in-line sensor 26 will erroneously place the pump 12 in an alarm mode or in a stop mode, as appropriate, thereby signalling to medical personnel that the infusion system requires attention. In response, medical personnel such as a nurse will check the infusion system to identify and remedy the problem. When the alarm is the result of a medically insignificant quantity of air or gas trapped within the sensor detection field, the present invention provides a simple and reliable apparatus and method for dislodging such air or gas from the sensor detection field so that system operation can be quickly and easily restarted.

FIG. 4 is a flow chart representing operation of each pumping channel of the infusion pump 12 (FIGS. 1 and 2), in conjunction with the apparatus and method of the present invention for quickly and easily clearing small quantities of air or gas from the detection field of an air-in-line sensor. FIGS. 5-8 are representative displays for a pump control panel 32, illustrating the apparatus and method of the present invention.

Figure 5:
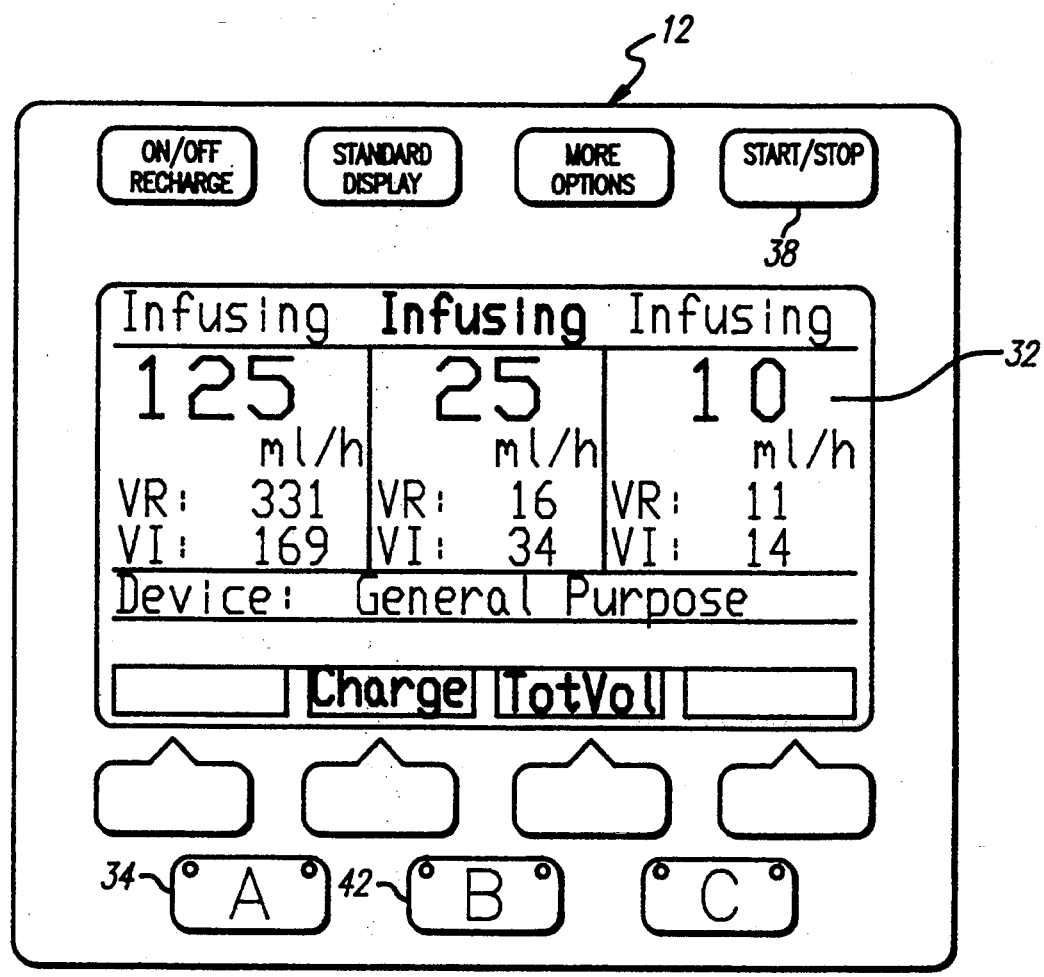
FIG. 5 is a front elevational view of a control panel for the infusion pump of FIGS. 1 and 2, with the control panel illustrating normal pump operation for delivering fluid via multiple pump channels.

More specifically, with reference to FIG. 4, the infusion system 10 is normally operated to deliver a medical liquid through a pump element 24 and past an air-in-line sensor 26 to a patient. FIG. 5 illustrates a representative information display of the liquid crystal type (LCD) for the control panel 32, particularly with respect to the MiniMed III pump which can be operated to infuse fluid to the patient with simultaneous operation of three parallel pumping channels identified by the letters "A", "B" and "C". Each channel can be individually programmed by medical personnel for independent operation in accordance with the specific medical fluids and the requirements of the patient.

Figure 6:
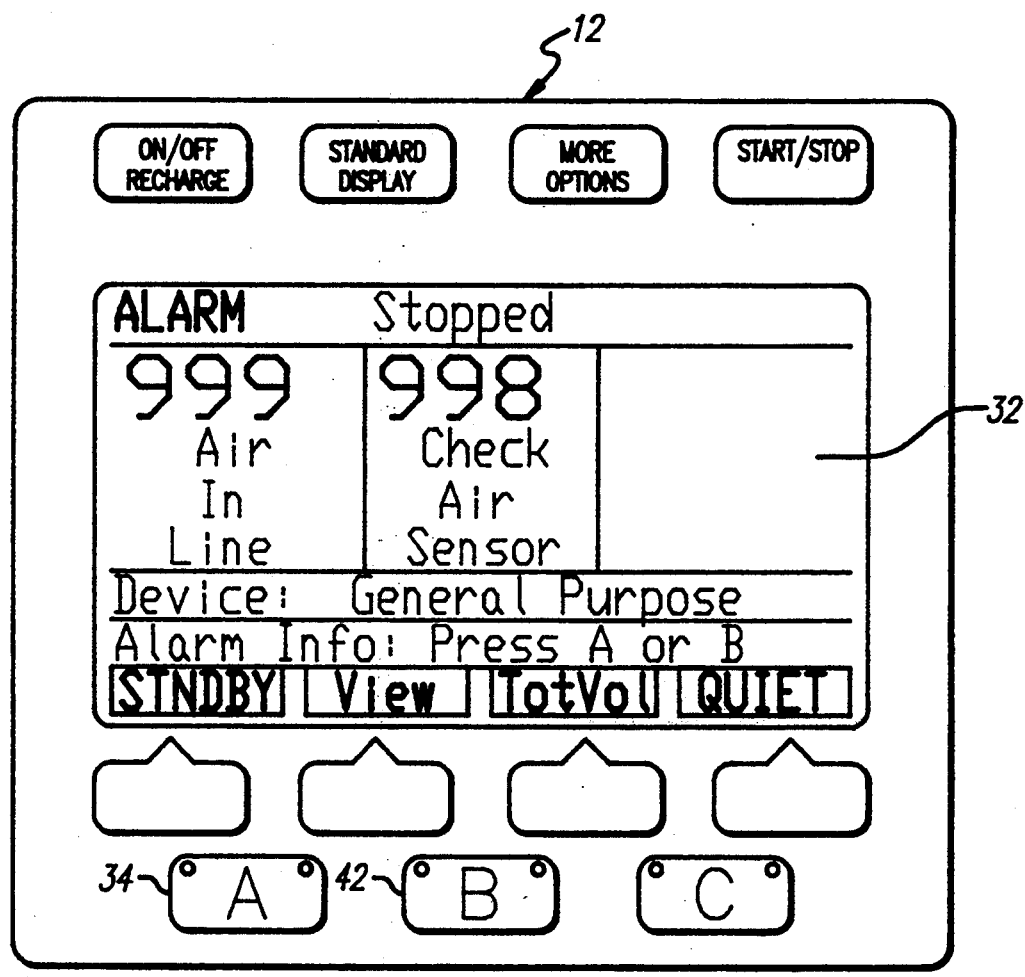
FIG. 6 is a front elevational view of the pump control panel similar to FIG. 5, but depicting one pump channel in an alarm mode and another pump channel in a stop mode.

When a threshold quantity of undissolved air or gas is detected within the detection field of the air-in-line sensor associated with one of the pumping channels, that sensor 26 signals the pump 12 to place the pumping channel in an alarm mode. FIG. 6 illustrates the pump control panel 32 indicating visually that channel "A" is in an alarm mode. An audio alarm is normally provided to generate a distinctive signal indicative of alarm mode status. Alternatively, if the detected air or gas volume is a higher predetermined quantity, the air-in-line sensor can signal the pump 12 to place the corresponding channel in a stop mode, as indicated by the control panel 32 in FIG. 6 with respect to pumping channel "B". In the stop mode, infusion pump operation for the associated channel is halted, typically in conjunction with activation of the audio alarm, as noted above.

When one of the pumping channels of the infusion pump 12 is in the alarm or stop modes, the pump alarm functions insure prompt attention by nursing or other medical personnel to resolve the problem so that normal pump infusion operation can be promptly resumed. As noted above, the problem may be attributable to an insignificant quantity of air or gas trapped within the detection field of the air-in-line sensor. Confirmation of such cause can be made rapidly by medical personnel upon mere inspection of the infusion tubing 14 within the sensor detection field. When this cause is present, it is necessary to clear the stuck bubble or bubbles from the detection field so that normal pump operation can be resumed.

Figure 7:
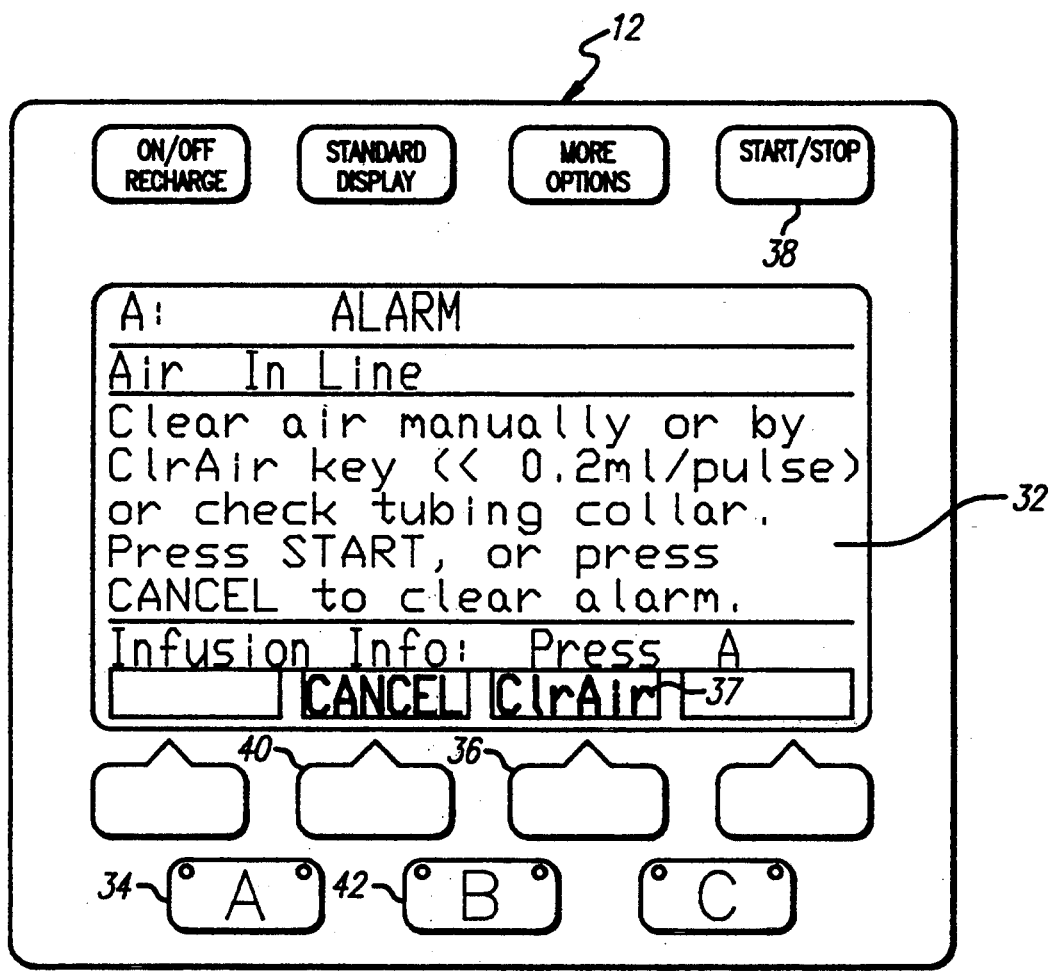
FIG. 7 is a front elevational view of the pump control panel and showing instructions or prompts for restarting a pump channel from an alarm mode.

FIG. 7 shows a control panel display which is presented upon depression of a master key 34 associated with pumping channel "A", when pumping channel "A" is in the alarm mode as depicted in FIG. 6. The panel display shown in FIG. 7 provides prompts or instructions to medical personnel for resolving the cause of the alarm and for restarting pump operation. One preferred resolution, particularly if an insignificant quantity of air or gas is present at the sensor 26, is to depress a "clear air" key 36 on the pump control panel 32. This "clear air" key is enabled when the pump is in the alarm or stop modes, and conveniently appears in the preferred form as a prompt 37 alongside the key 36 within the control panel display screen shown in FIG. 7. Depression of the "clear air" key 36 operates the pump to deliver a small output pulse or bolus at a high rate (typically 999 ml/hr) to the patient. This delivery of a small pulse of the infusion liquid, preferably about 0.2 milliliters or less, is often sufficient to dislodge and displace the trapped bubble or bubbles to a position downstream from the sensor detection field. However, for most medical infusion fluids and/or most patients, the delivery of the small output pulse is not a sufficient variation from the programmed fluid delivery rate to present any medical concerns.

Subsequent to depression of the "clear air" key 36, and following the instructions on the display panel 32 (FIG. 7), a pump start key 38 is depressed by the medical attendant in an attempt to restart normal pump operation. If the detected air or gas has been dislodged from the sensor detection field, such depression of the start key 38 will return the display information to the previous screen, for example, the normal operation screen of FIG. 5 if no other channels are in the alarm or stop modes. The attendant can then press a quiet key 40 to clear the audio alarm function (FIG. 7).

If depression of the start key 38 fails to restart normal pump operation, this failure is due to continued presence of the air or gas bubbles within the detection field of the air-in-line sensor 26. In this condition, the pump 12 can be programmed to enable or permit depression of the "clear air" key 36 a second time and/or a selected additional number of times to deliver one or more additional small fluid pulses from the pump. For example, in a typical adult patient and medical infusion environment, the pump 12 is preferably programmed to permit depression of the "clear air" key 36 up to five or six times in an attempt to dislodge air or gas from the sensor detection field. If the pump is not restarted, despite following of the foregoing procedure, other manual remedial steps can be taken to dislodge the air and to restart the pump. Alternately, manual remedial action can be taken at the outset of the alarm mode condition, at the option of attending personnel.

Figure 8:
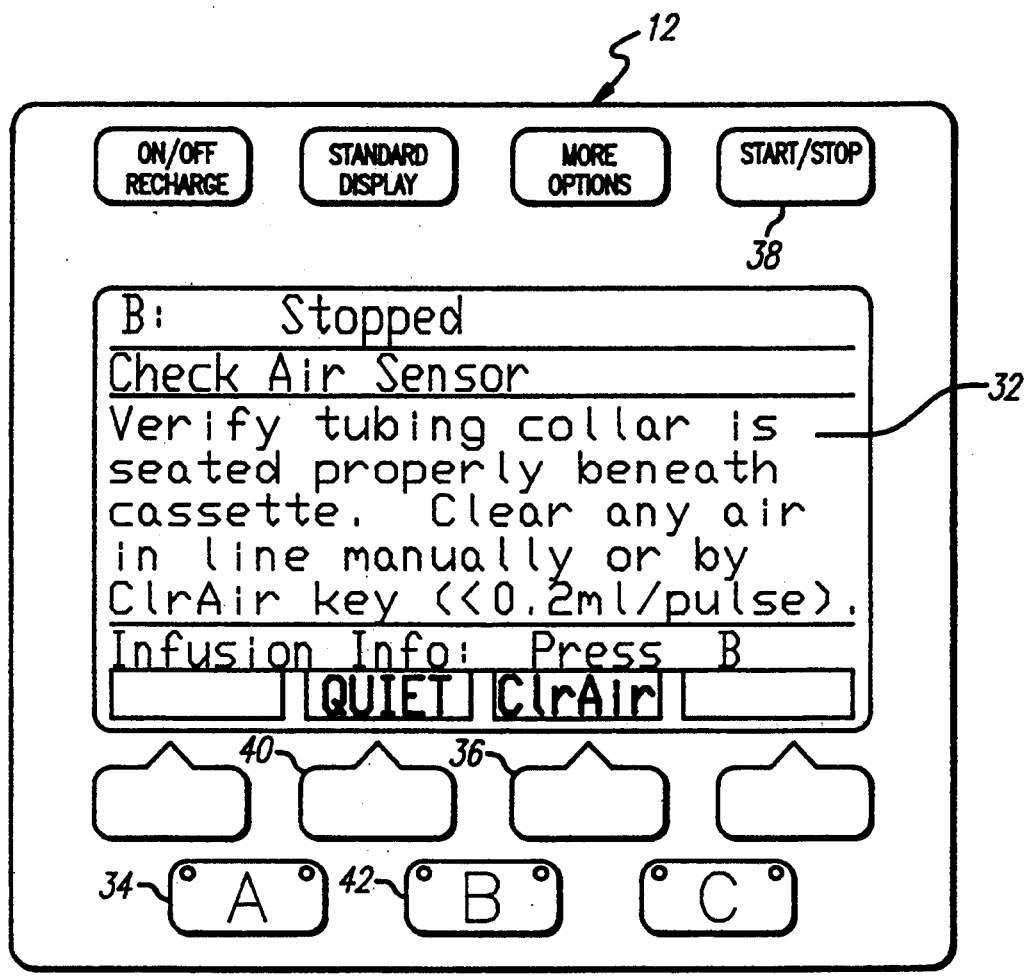
FIG. 8 is a front elevational view of the pump control panel and showing prompts for restarting a pump channel from a stop mode.

FIG. 8 illustrates a similar sequence of remedial steps to be taken when a Dumping channel is in the stop mode, as represented by pumping channel "B" in FIG. 6. Depression of a master key 42 associated with channel "B" activates the panel display 32 shown in FIG. 8, with appropriate instructions for depression of the now-enabled "clear air" key 36 to resolve the cause of channel stoppage. The clear air key can be depressed one or more times, with such depression followed by corresponding attempts to restart the infusion pump by depression of the start key 38. Once again, if this procedure fails to restart the pump due to continued detection of air at the sensor detection field, the air can be dislodged following traditional manual procedure.

The present invention thus provides a relatively simple apparatus and method for quickly and easily dislodging small quantities of air stuck within the detection field of an air-in-line sensor in a medical fluid infusion system. Such detected air or gas is dislodged and moved from the sensor detection field by delivering one or more small pulses of the infusion fluid from the pump. While the pump is normally adapted for maintaining an accumulated fluid infusion record to track the quantity and rate of fluid infusion to a patient, and detected volumes of air or gas may be decremented from this infusion record, the pump can be further programmed to add to the infusion record each small fluid pulse delivered upon depression of the "clear air" key 36.

A variety of modifications and improvements to the invention described further herein will be apparent to persons skilled in the art. For example, while the invention is shown with respect to a programmable pump 12 having a sequence of control panel screens associated with button keys or switches which may have different functions according to the control panel screen being displayed, it will be understood that the "clear air" key and its associated clear air function can be embodied in different pump configurations such as the provision of a dedicated "clear air" key. Accordingly, no limitation on the invention is intended by way of the foregoing description and accompanying drawings, except as set forth in the appended claims.

What is claimed is:

1. A medication infusion pump, comprising:
   pump means for delivering a selected therapeutic liquid to an infusion line under controlled flow conditions for infusion to a patient;
   an air-in-line sensor associated with said pump means, the air-in-line sensor having a detection field configured to receive a short length of the infusion line and comprising means for detecting gas bubbles within the short length of infusion line, and alarm means for responding to a detection of gas bubbles within the infusion line by said means for detecting to activate an alarm; and
   manually actuated means for operating said pump means to deliver an output pulse of the therapeutic liquid to the short length of the infusion line to dislodge and move gas bubbles detected within the detection field along the infusion line to a position downstream of the detection field.

2. A medication infusion pump as defined in claim 1, wherein said air-in-line sensor comprises:
   means for generating an alarm signal in response to detection of a predetermined gas volume;
   and wherein said alarm means is activated in response to said alarm signal, for enabling the manual actuation of said manually actuated means at least one time whenever said alarm means is activated.

3. A medication infusion pump as defined in claim 2, wherein said pump means additionally comprises:
   means for limiting the number of times said manually actuated means can be actuated.

4. A medication infusion pump as defined in claim 1, wherein said pump means comprises:
   a housing with a control panel thereon, said manually actuated means comprising a depressible key located on said control panel.

5. A medication infusion pump as defined in claim 1, wherein said pump means comprises:
   means for maintaining an accumulated fluid infusion record, said pump means further comprising means for adding each output pulse delivered from said pump means to said record.

6. A medication infusion pump, comprising:
   programmable pump means for delivering a selected medical liquid to an infusion line under controlled flow conditions for infusion to a patient;
   air-in-line sensor means, associated with said pump means, for detecting undissolved gas within the infusion line, said sensor means having a detection field configured to receive a short length of the infusion line, and the sensor means also for activating an alarm when the amount of undissolved gas detected within said detection field exceeds a predetermined minimum volume; and
   said pump means further comprising manual switch means for operating said pump means to deliver an output pulse of a predetermined volume of the medical liquid to the infusion line to dislodge and move undissolved gas through the infusion line to a position downstream of the detection field.

7. A medication infusion pump as defined in claim 6, additionally comprising:
   means for enabling actuation of said manual switch means at least one time whenever said alarm is activated.

8. A medication infusion pump as defined in claim 7, further comprising:
   means for selectively limiting the number of times said manual switch means can be actuated to deliver said output pulse.

9. A medication infusion pump as defined in claim 6, wherein said pump means comprises:
   means for maintaining an accumulated fluid infusion record, said pump means further comprising means for adding each output pulse delivered from said pump means to said record.

10. An infusion system for delivering a selected medical liquid to a patient, said system comprising:
    an infusion line;
    an infusion pump operating on the infusion line for delivery of a medical liquid through said infusion line to the patient under controlled flow conditions;
    an air-in-line sensor, associated with said infusion pump, said sensor having a detection field engaged with a short length of said infusion line, said sensor comprising means for detecting when a volume of undissolved gas is present within said short length of the infusion line and for generating an air-in-line signal when the volume of undissolved gas is detected by the means for detecting and exceeds a predetermined minimum level;
    alarm means responsive to said air-in-line signal to indicate that a volume of undissolved gas exceeding the predetermined minimum level has been detected within said short length of the infusion line; and
    manual switch means for operating said pump to deliver at least one small output pulse of the medical liquid to said infusion line to dislodge and move the volume of undissolved gas to a position downstream of said detection field.

11. An infusion system as defined in claim 10, wherein said alarm means comprises:
    means responsive to said air-in-line signal to halt operation of said pump.

12. An infusion system as defined in claim 10, wherein said sensor comprises:
    means for generating a first air-in-line signal when the volume of the undissolved gas exceeds said predetermined minimum level, and a second air-in-line signal when the volume of the undissolved gas exceeds a higher predetermined maximum level, said alarm means being responsive to said first signal to activate an alarm indicator, said alarm means being responsive to said second signal to halt operation of said pump.

13. An infusion system as defined in claim 10, further comprising:
    means for enabling manual operation of said manual switch means at least one time when said alarm means indicates that the volume of undissolved gas within said short length of the infusion line has been detected.

14. An infusion system as defined in claim 10, further comprising:
    means for selectively limiting the number of times said manual switch means can be operated to deliver said output pulse.

15. An infusion system as defined in claim 10, wherein said pump comprises:

a housing with a control panel thereon, said manual switch means comprising a depressible key located on said control panel.

16. An infusion system as defined in claim 10, further comprising:

infusion record means for maintaining an accumulated record of medical liquid delivered to the patient, said infusion record means comprising means for adding each output pulse to said record.

* * * * *